(12) United States Patent
Hibbs

(10) Patent No.: US 6,834,548 B1
(45) Date of Patent: Dec. 28, 2004

(54) METHOD AND APPARATUS FOR REDUCTION OF HIGH-FREQUENCY VIBRATIONS IN THICK PELLICLES

(75) Inventor: Michael S. Hibbs, Westford, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/250,255

(22) Filed: Jun. 18, 2003

(51) Int. Cl.$^7$ .................................................. G01N 29/04
(52) U.S. Cl. ............................ 73/579; 73/599; 73/602
(58) Field of Search .................... 73/579, 599, 600, 73/602, 432.1, DIG. 1, 584; 381/56; 702/56; 250/492.2; 200/280; 355/30, 53, 55, 77

(56) References Cited

U.S. PATENT DOCUMENTS

| | | | |
|---|---|---|---|
| 3,842,353 A | * 10/1974 | Stewart | 324/109 |
| 4,525,791 A | * 7/1985 | Hagiwara et al. | 700/280 |
| 4,737,824 A | 4/1988 | Sakai et al. | 355/53 |
| 5,155,523 A | * 10/1992 | Hara et al. | 355/53 |
| 5,226,326 A | * 7/1993 | Polen et al. | 73/571 |
| 5,422,704 A | 6/1995 | Sego | 355/53 |
| 6,002,987 A | * 12/1999 | Kamiya et al. | 702/56 |
| 6,101,237 A | 8/2000 | Miyachi et al. | 378/35 |
| 6,200,022 B1 | * 3/2001 | Hammiche et al. | 374/46 |
| 6,318,159 B1 | * 11/2001 | Chen et al. | 73/105 |
| 6,337,161 B2 | 1/2002 | Chiba et al. | 430/5 |
| 6,477,898 B1 | * 11/2002 | Han et al. | 73/579 |
| 6,524,754 B2 | 2/2003 | Eynon | 430/5 |

FOREIGN PATENT DOCUMENTS

| | | |
|---|---|---|
| JP | 3050819 A | 3/1991 |
| JP | 9260279 A | 10/1997 |
| JP | 9265137 A | 10/1997 |

* cited by examiner

*Primary Examiner*—Hezron Williams
*Assistant Examiner*—Jacques M. Saint-Surin
(74) *Attorney, Agent, or Firm*—DeLio & Peterson LLC; Peter W. Peterson; Richard M. Kotulak

(57) ABSTRACT

A method of reducing sound-induced vibrations in pellicles used in lithographic production of microelectronic features comprises providing a pellicle for protecting a photomask, monitoring background sound in the vicinity, or vibration, of the pellicle, providing opposing sound waves to the background sound, and causing the opposing sound waves to strike the pellicle to substantially cancel vibrations due to the background sound or vibration. When the background sound strikes the pellicle on one surface of the pellicle, the opposing sound waves may strike the pellicle on the opposing surface of the pellicle, and may be provided with substantially the same frequency and amplitude in the same phase to the background sound. Alternatively, opposing sound waves may strike the pellicle on the same surface of the pellicle as the background sound waves, may be provided with substantially the same frequency and amplitude in opposing phase to the background sound.

29 Claims, 2 Drawing Sheets

METHOD AND APPARATUS FOR REDUCTION OF HIGH-FREQUENCY VIBRATIONS IN THICK PELLICLES

BACKGROUND OF INVENTION

1. Field of the Invention

The present invention relates generally to pellicles employed to protect a mask used in lithographic production of microelectronic circuits or other features and, more particularly, to a method and apparatus for reduction of high frequency, sound-induced vibrations in thick pellicles.

2. Description of Related Art

Pellicles are thin, optically transparent membranes that are used in photolithography to protect patterned photomask surfaces from contamination by airborne particles. The pellicles are conventionally attached to the photomask by a metal frame. Conventional pellicles are made of organic or fluorocarbon polymers. Conventional pellicles are so thin (approximately 0.5 to 2.0 î ¼ m) that they do not introduce any appreciable optical distortion to the light passing through them, even if the pellicle is physically distorted from an ideal flat shape.

An emerging photolithography technique is the use of radiation having a 157 nanometer (nm) wavelength to expose the desired circuit pattern from the photomask to the resist layer on the wafer substrate. Current organic polymers available for the fabrication of thin (0.5 to 2.0 î ¼ m) protective pellicles used at 365 nm, 248 nm, and 193 nm exposure wavelengths are either not transparent enough or not durable enough to withstand more than a few minutes of exposure without severe degradation at the 157 nm exposure wavelength. Unfortunately, no polymers have been found with sufficient radiation durability to be used as pellicles to protect photomasks from contamination at the 157 nm exposure-wavelength. For this reason, thick or hard plate pellicles have been proposed for use at this exposure wavelength. A thick plate pellicle may include a flat, polished piece of fused silica, or fluorinated fused silica, typically 100 to 1000 î ¼ m thick.

Unfortunately, a thick pellicle can induce many types of undesirable optical aberrations. In particular, any change of shape of the pellicle caused by gravitational sag, aerodynamic forces, or vibration will cause the pellicle-induced optical aberrations to change. Because step-and-scan exposure methods scan the mask at high speeds during exposure, a photomask may be subject to relatively high noise levels in a stepper. It has been found that even a thick pellicle will vibrate in response to the sound waves hitting it. The vibration-induced displacement of the mask can cause image distortions that will degrade the accuracy of the image placement on the wafer.

U.S. patent application Ser. No. 09/683,748 filed Feb. 11, 2002 discloses solutions to the distortions caused by gravitational sag and aerodynamic forces, but the methods taught therein are not directed to control of higher frequency distortions caused by sound. There consequently is a need for a method and apparatus for correcting sound-induced vibration of thick pellicles.

SUMMARY OF INVENTION

Bearing in mind the problems and deficiencies of the prior art, it is therefore an object of the present invention to provide a method and apparatus for correcting sound-induced vibration of pellicles used to protect photomasks.

It is another object of the present invention to provide a method and apparatus for correcting sound-induced vibration of pellicles having a thickness in the range of 100–1000 î ¼ m.

A further object of the invention is to provide a method and apparatus for correcting sound-induced vibration of pellicles which is particularly useful for steppers using a 157 nm exposure wavelength.

Still other objects and advantages of the invention will in part be obvious and will in part be apparent from the specification.

The above and other objects, which will be apparent to those skilled in art, are achieved in the present invention which is directed to a method of reducing sound-induced vibrations in pellicles used in lithographic production of microelectronic features comprising providing a pellicle for protecting a photomask, monitoring background sound in the vicinity, or vibration, of the pellicle, providing opposing sound waves to the background sound, and causing the opposing sound waves to strike the pellicle to substantially cancel vibrations due to the background sound or vibration.

The pellicle has opposing surfaces, so that when the background sound strikes the pellicle on one surface of the pellicle, the method may provide that opposing sound waves may strike the pellicle on the opposing surface of the pellicle. The monitoring of the background sound may comprise determining frequency, amplitude and phase of the background sound, and the opposing sound waves may be provided with substantially the same frequency and amplitude in the same phase to the background sound.

Alternatively, when the background sound strikes the pellicle on one surface of the pellicle, the method provides that opposing sound waves may strike the pellicle on the same surface of the pellicle. The monitoring of the background sound may comprise determining frequency, amplitude and phase of the background sound, and the opposing sound waves may be provided with substantially the same frequency and amplitude in opposing phase to the background sound.

Preferably, the pellicle is mounted to a photomask to create a substantially sealed interior gap between the pellicle and photomask, and the opposing sound waves are directed into the substantially sealed interior gap to strike the pellicle and substantially cancel any sound-induced vibrations of the pellicle.

The opposing sound waves may be created by a speaker coupled to a space adjacent a surface of the pellicle, or by a speaker coupled to a sealed space between the pellicle and a photomask.

The background sound may be monitored by a microphone detecting the background sound adjacent a surface of the pellicle, or by measuring vibration of a surface of the pellicle as a result of the background sound striking the pellicle surface.

In another aspect, the present invention provides an apparatus for reducing sound-induced vibrations in pellicles used in lithographic production of microelectronic features comprising a mounting structure for coupling a pellicle to a photomask, a monitor for monitoring background sound in the vicinity of the pellicle or directly monitoring sound-induced vibrations of the pellicle, and a sound generator in the vicinity of the pellicle for generating opposing sound waves to the background sound, the sound generator being adapted to cause the opposing sound waves to strike the pellicle to substantially cancel vibrations due to the background sound.

The pellicle has opposing surfaces, and the monitor may be adjacent one surface of the pellicle and the sound generator may be adjacent the opposing surface of the pellicle. The sound generator may be adapted to determine frequency, amplitude and phase of the background sound, and provide opposing sound waves with substantially the same frequency and amplitude in the same phase to the background sound.

Alternatively, the monitor and the sound generator are adjacent the same surface of the pellicle. The sound generator may be adapted to determine frequency, amplitude and phase of the background sound, and provide opposing sound waves with substantially the same frequency and amplitude in opposing phase to the background sound.

Preferably, the mounting structure is sealed to create a substantially sealed interior gap between the pellicle and photomask, and the sound generator is coupled to the mounting structure to direct opposing sound waves into the substantially sealed interior gap to strike the pellicle and substantially cancel the background sound vibrations.

The sound generator may include a speaker coupled to a space adjacent a surface of the pellicle to create opposing sound waves, or may include a speaker coupled to a sealed space between the pellicle and a photomask to create opposing sound waves.

The monitor may comprise a microphone detecting the background sound adjacent a surface of the pellicle, or a monitor adapted to measure vibration of a surface of the pellicle as a result of the background sound striking the pellicle surface.

The method and apparatus of the present invention are most useful when the background sound and the opposing sound have a frequency above 1 Hz.

BRIEF DESCRIPTION OF DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION

In describing the preferred embodiment of the present invention, reference will be made herein to FIGS. 1 and 2 of the drawings in which like numerals refer to like features of the invention.

Figure 1:
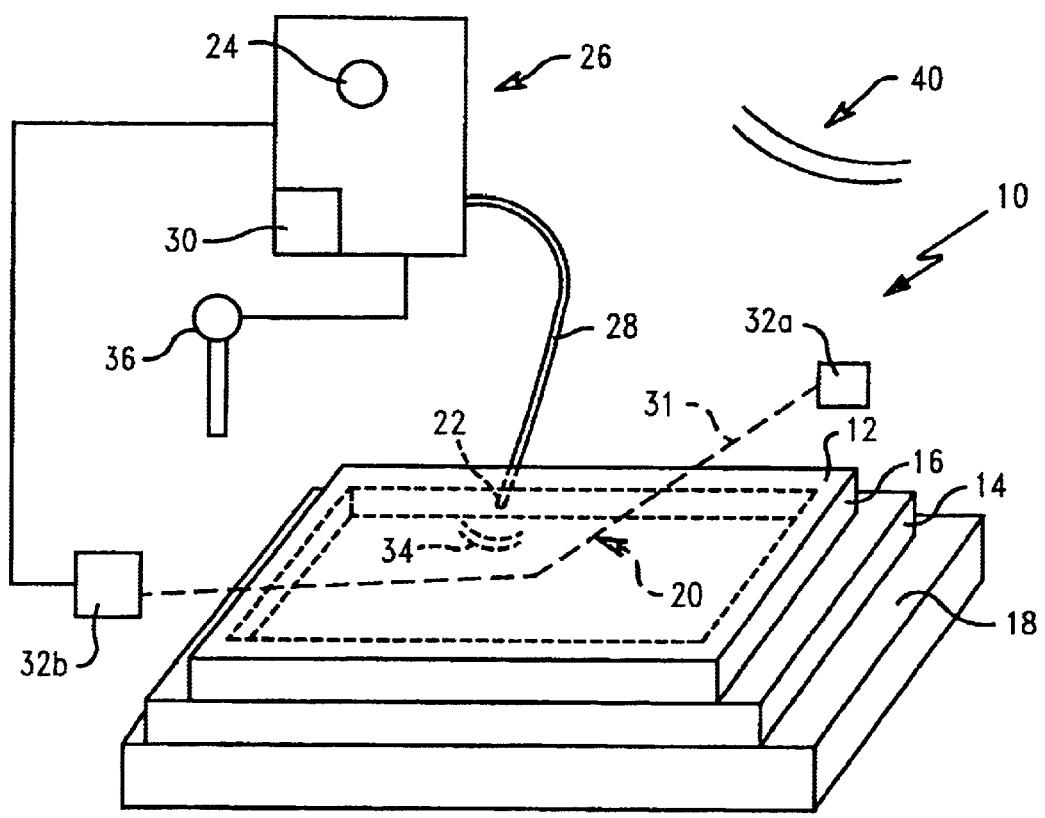
FIG. 1 is a perspective view of a preferred embodiment of the present invention showing the pellicle mounting system, vibration monitor and sound generator coupled to a sealed space below the pellicle.
Figure 2:
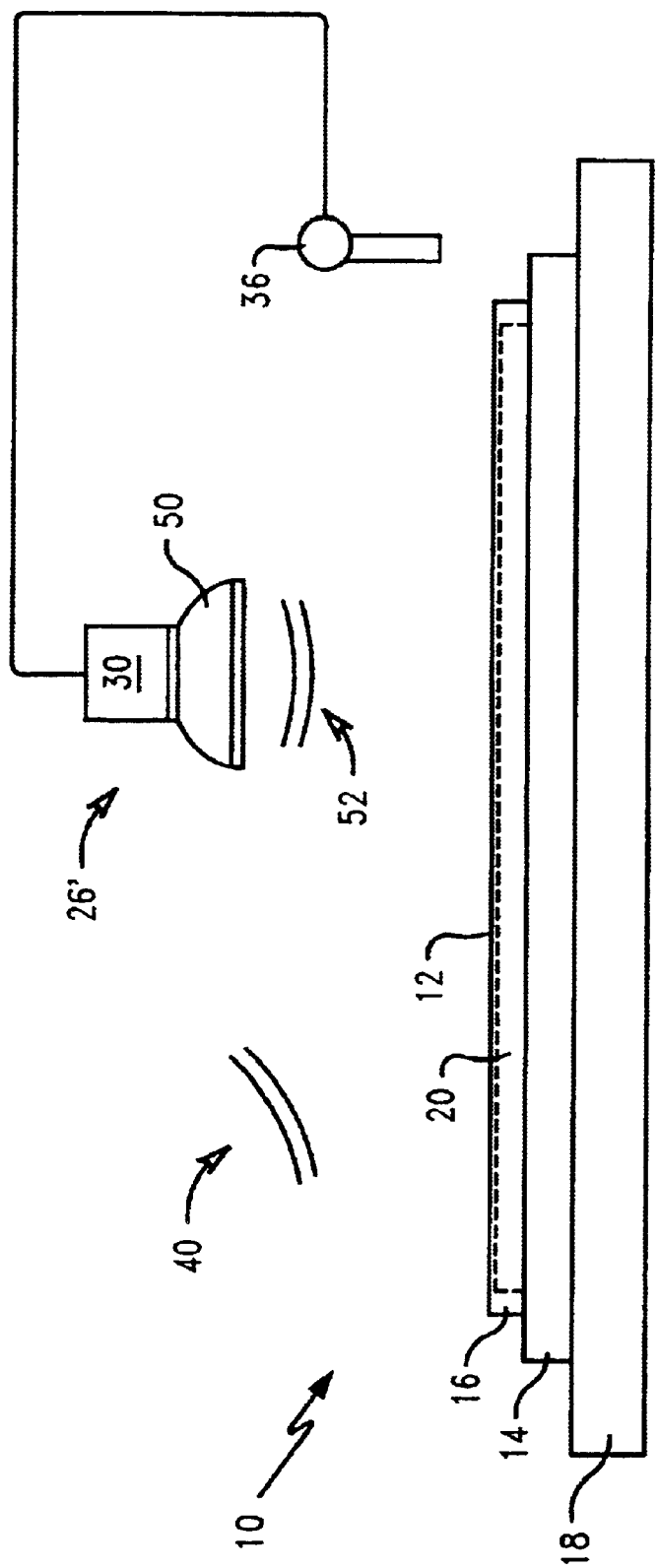
FIG. 2 is a an elevational view of an alternate embodiment of the present invention showing the pellicle mounting system, vibration monitor and sound generator above the pellicle.

Referring to FIGS. 1 and 2, there is shown a preferred mounting system 10 for mounting a rectangular pellicle 12 over a mask 14 in accordance with the present invention. While the present invention is directed in particular to silica pellicles having a thickness in the range of 100–1000 Î ¼ m, pellicles of other size and thickness may benefit from the system described herein. Mounting system 10 may couple to a scanning exposure system (not shown) by a movable stage 18. Mounting system 10 includes a mounting structure 16 for coupling pellicle 12 to mask 14, and extends around the periphery of the pellicle. Mounting structure 16 may be made of aluminum or other metals, fused silica, ceramic, or any other rigid, stable material and provides a seal between pellicle 12 and mask 14 in any well known fashion, for example, using adhesives. As a result, a sealed interior portion 20 is formed between pellicle 12, mask 14 and mounting structure 16. This cavity may be filled with any gas, but for purposes of explanation, air will, be used as an example. Undesirable sound waves 40, generated by the scanning equipment used in the lithographic production of microelectronic circuits, or other noise external sources, strike pellicle 12 and cause vibrational distortion thereof. Such undesirable environmental background sound generally has a frequency above 1 Hz, and is typically in the range of 1 Hz to 20000 Hz.

Preferably, in accordance with the present invention, sound induced distortion to the pellicle may be controlled by inducing vibrations in the air cavity 20 enclosed beneath the pellicle with the frequency, amplitude, and phase required to exactly cancel the sound vibrations coming from the external environment. The induced, opposing vibrations may be generated by a speaker in an external enclosure, coupled to the pellicle frame by a tube. In FIGS. 1 and 2, a port 22 is provided on mounting structure 16 through which opposing sound waves 34 may be transferred into interior portion 20. The opposing sound waves are generated by speaker 24 in a sound wave generator 26, and the opposing sound waves transferred therefrom to cavity 20 via sound tube 28 and port 22. The electrical signals sent to the speaker are generated by an analog or digital electronic circuit 30. The input used to determine the opposing sound waves is received from a feedback system including a position sensor to detect the dynamic position of pellicle 12 so that vibration of the pellicle may be reduced or eliminated entirely. The sensor is capable of responding to sound frequencies, such as those in the 1 Hz to 20000 Hz range, and may take any of a number of forms.

In a first embodiment of the present invention, the position of the pellicle 12 surface is directly monitored by the sensor. The sensor may be in the form of a reflected laser beam including, for example, a transmitter 32a and a receiver 32b. It may also be provided as a capacitive sensor, a mechanical linkage, or any other now known or later developed position sensor. The signal from the vibration sensors 32a, 32b is fed to circuit 30 so that electrical signals can be dynamically generated to create opposing sound waves 34. These signals cause a displacement of the speaker cone to generate sound waves 34 of substantially the same frequencies and amplitudes, and in-phase with the unwanted sound waves 40, sufficient to maintain pellicle 12 at its original position, unaffected by incoming vibrations from the external environment. Circuit 30 maintains the substantially in-phase relationship between the unwanted sound waves 40 and the generated sound waves 34, correcting if necessary for any additional phase lag induced by transmission of the generated sound waves through the connecting tube 28. The position of vibration sensors 32a, 32b and the number of vibration sensors can be adjusted to provide optimal performance based on the particulars of mounting system 10. Preferably, sensors 32a and 32b are mounted to the side of the pellicle, away from the area of transmission of the light or other energy beam, so as not to block the beam, while ensuring that laser beam 31 is reflected off the pellicle 12 surface close to its middle.

In a second embodiment of the present invention, the sound vibrations in the external environment may be sensed by microphone 36 mounted to any stable structure (not shown) adjacent to and above the plane of pellicle 20. The signal from the microphone is then sent to electronic circuit 30 that drives speaker 24 to provide power to the speaker and generate compensating, opposite, in-phase vibrations 34 in the space 20 under the pellicle in such a way as to cancel the original sound vibrations 40. Noise cancellation technology is well-known and is available commercially in stereo headphones designed to be worn in airplanes or other noisy environments, or simply to provide a quiet area around the user's ears in noisy surrounding. However, unlike the prior technology, the opposing vibrations provided beneath pellicle 12, on the surface opposite the source of unwanted sound waves 40, is in-phase with sound waves 40, rather than out-of-phase. In both embodiments, interior portion 20 is preferably in continuous communication with generator 26 creating the opposing sound waves 34.

The preferred embodiments of the present invention allow sound waves to strike the surface of the pellicle, but supply equivalent, in-phase vibrations to the underside of the pellicle to counteract the forces from the external sound wave. In another embodiment of the present invention, as shown in FIG. 2, opposing sound generator 26' employs a speaker 50 placed in the environment above pellicle 12, on the same side as the source of unwanted sound waves 40. Conventional noise-reduction technology may be used to create a quiet zone above the pellicle by receiving a vibrational signal from microphone 36 and feeding back the signal to circuit 30 to generate opposing sound waves. In this embodiment, speaker 50 instead provides out-of-phase vibrations 52 to the top side of the pellicle to cancel the unwanted incoming environmental noise 40, before the sound waves actually strike the upper surface of pellicle 12.

Thus, the present invention provide a method and apparatus for correcting sound-induced vibration of pellicles used to protect photomasks, which meets a need previously unrecognized and unmet. The method and apparatus of the invention is particularly useful for steppers using a 157 nm exposure wavelength and pellicles having a thickness in the range of 100–1000 Î ¼ m.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of reducing sound-induced vibrations in pellicles used in lithographic production of microelectronic features comprising:
   providing a photomask;
   providing a pellicle for protecting the photomask, the pellicle being optically transparent and spaced from the photomask;
   monitoring background sound in the vicinity, or vibration, of the pellicle;
   providing opposing sound waves to the background sound; and
   causing the opposing sound waves to strike the pellicle to substantially cancel vibrations due to the background sound.

2. The method of claim 1 wherein the pellicle has opposing surfaces and wherein the background sound strikes the pellicle on one surface of the pellicle and the opposing sound waves strike the pellicle on the opposing surface of the pellicle.

3. The method of claim 1 wherein the pellicle has opposing surfaces and wherein the background sound strikes the pellicle on one surface and the opposing sound waves strike the pellicle on the same surface of the pellicle.

4. The method of claim 1 wherein monitoring background sound comprises determining frequency, amplitude and phase of the background sound, and wherein the opposing sound waves are provided with substantially the same frequency and amplitude in the same phase to the background sound.

5. The method of claim 1 wherein monitoring background sound comprises determining frequency, amplitude and phase of the background sound, and wherein the opposing sound waves are provided with substantially the same frequency and amplitude in opposing phase to the background sound.

6. The method of claim 1 wherein the pellicle is mounted to a photomask to create a substantially sealed interior gap between the pellicle and photomask, and the opposing sound waves are directed into the substantially sealed interior gap to strike the pellicle and substantially cancel any sound-induced vibrations of the pellicle.

7. The method of claim 1 wherein the opposing sound waves are created by a speaker coupled to a space adjacent a surface of the pellicle.

8. The method of claim 1 wherein the opposing sound waves are created by a speaker coupled to a sealed space between the pellicle and a photomask.

9. The method of claim 1 wherein the background sound is monitored by a microphone detecting the background sound adjacent a surface of the pellicle.

10. The method of claim 1 wherein the background sound is monitored by measuring vibration of a surface of the pellicle as a result of the background sound striking the pellicle surface.

11. The method of claim 1 wherein the background sound and the opposing sound have a frequency above 1 Hz.

12. An apparatus for reducing sound-induced vibrations in pellicles used in lithographic production of microelectronic features comprising:
   a photomask;
   a pellicle mounted to the photomask, the pellicle being optically transparent and spaced from the photomask;
   a monitor for monitoring background sound in the vicinity of the pellicle or directly monitoring sound-induced vibrations of the pellicle; and
   a sound generator in the vicinity of the pellicle for generating opposing sound waves to the background sound, the sound generator adapted to cause the opposing sound waves to strike the pellicle to substantially cancel vibrations due to the background sound.

13. The apparatus of claim 12 wherein the pellicle has opposing surfaces and wherein the monitor is adjacent one surface of the pellicle and the sound generator is adjacent the opposing surface of the pellicle.

14. The apparatus of claim 12 wherein the pellicle has opposing surfaces and wherein the monitor and the sound generator are adjacent the same surface of the pellicle.

15. The apparatus of claim 12 wherein the sound generator is adapted to determine frequency, amplitude and phase of the background sound, and provide opposing sound waves with substantially the same frequency and amplitude in the same phase to the background sound.

16. The apparatus of claim 12 wherein the sound generator is adapted to determine frequency, amplitude and phase of the background sound, and provide opposing sound waves with substantially the same frequency and amplitude in opposing phase to the background sound.

17. The apparatus of claim 12 wherein the mounting structure is sealed to create a substantially sealed interior gap between the pellicle and photomask, and the sound generator is coupled to the mounting structure to direct opposing sound waves into the substantially sealed interior gap to strike the pellicle and substantially cancel the background sound vibrations.

18. The apparatus of claim 12 wherein the sound generator includes a speaker coupled to a space adjacent a surface of the pellicle to create opposing sound waves.

19. The apparatus of claim 12 wherein the sound generator includes a speaker coupled to a sealed space between the pellicle and a photomask to create opposing sound waves.

20. The apparatus of claim 12 wherein the monitor comprises a microphone detecting the background sound adjacent a surface of the pellicle.

21. The apparatus of claim 12 wherein the monitor comprises a monitor adapted to measure vibration of a surface of the pellicle as a result of the background sound striking the pellicle surface.

22. The method of claim 1 wherein the pellicle comprises silica having a thickness of about 100–1000 microns.

23. The apparatus of claim 12 wherein the pellicle comprises silica having a thickness of about 100–1000 microns.

24. A method of reducing sound-induced vibrations in pellicles used in lithographic production of microelectronic features comprising:
providing a photomask;
providing a pellicle having opposing surfaces for protecting the photomask;
mounting the pellicle to the photomask to create a substantially sealed interior gap between the pellicle and photomask;
monitoring background sound in the vicinity of the pellicle, the background sound striking the pellicle on the surface away from the photomask;
providing opposing sound waves to the background sound; and
directing the opposing sound waves into the substantially sealed interior gap to strike the pellicle on the surface toward the photomask to substantially cancel vibrations due to the background sound.

25. The method of claim 24 wherein monitoring background sound comprises determining frequency, amplitude and phase of the background sound, and wherein the opposing sound waves are provided with substantially the same frequency and amplitude in the same phase to the background sound.

26. A method of reducing sound-induced vibrations in pellicles used in lithographic production of microelectronic features comprising:
providing a photomask;
providing a pellicle having opposing surfaces for protecting the photomask;
mounting the pellicle to the photomask to create a substantially sealed interior gap between the pellicle and photomask;
monitoring vibration of the pellicle;
providing opposing sound waves to the vibration; and
directing the opposing sound waves into the substantially sealed interior gap to strike the pellicle on the surface toward the photomask to substantially cancel the vibrations.

27. An apparatus for reducing sound-induced vibrations in pellicles used in lithographic production of microelectronic features comprising:
a photomask;
a pellicle having opposing surfaces mounted to the photomask, with a substantially sealed interior gap between the pellicle and photomask;
a monitor for monitoring background sound in the vicinity of the pellicle, the background sound striking the pellicle on the surface away from the photomask; and
a sound generator in the vicinity of the pellicle for generating opposing sound waves to the background sound, the sound generator adapted to direct the opposing sound waves into the substantially sealed interior gap to strike the pellicle on the surface toward the photomask to substantially cancel vibrations due to the background sound.

28. The apparatus of claim 27 wherein the sound generator is adapted to determine frequency, amplitude and phase of the background sound, and provide opposing sound waves with substantially the same frequency and amplitude in the same phase to the background sound.

29. An apparatus for reducing sound-induced vibrations in pellicles used in lithographic production of microelectronic features comprising:
a photomask;
a pellicle having opposing surfaces mounted to the photomask, with a substantially sealed interior gap between the pellicle and photomask;
a monitor for directly monitoring sound-induced vibrations of the pellicle; and
a sound generator in the vicinity of the pellicle for generating opposing sound waves to the background sound, the sound generator adapted to direct the opposing sound waves into the substantially sealed interior gap to strike the pellicle on the surface toward the photomask to substantially cancel the vibrations.

* * * * *